(12) United States Patent
Nagai (10) Patent No.: US 12,196,674 B2
(45) Date of Patent: Jan. 14, 2025

(54) DETECTION DEVICE AND DETECTION METHOD

(71) Applicant: OTSUKA PHARMACEUTICAL CO., LTD., Tokyo (JP)

(72) Inventor: Fumio Nagai, Tokyo (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 423 days.

(21) Appl. No.: 17/625,861

(22) PCT Filed: May 1, 2020

(86) PCT No.: PCT/JP2020/018447
§ 371 (c)(1),
(2) Date: Jun. 17, 2022

(87) PCT Pub. No.: WO2021/009995
PCT Pub. Date: Jan. 21, 2021

(65) Prior Publication Data
US 2023/0184676 A1  Jun. 15, 2023

(30) Foreign Application Priority Data
Jul. 12, 2019  (JP) .................................. 2019-130432

(51) Int. Cl.
*G01N 21/552* (2014.01)
(52) U.S. Cl.
CPC ................... *G01N 21/553* (2013.01)
(58) Field of Classification Search
CPC .... G01N 21/553; G01N 21/648; G01N 21/41; G01N 21/13; G01N 33/54373; G01N 2021/8455
See application file for complete search history.

(56) References Cited

U.S. PATENT DOCUMENTS 9,012,872 B1 *  4/2015  Fang .................. G01N 21/6428
250/461.2
9,535,004 B2  1/2017  Noda et al.
(Continued)

FOREIGN PATENT DOCUMENTS

EP    2623958 A1    8/2013
JP    2015-59803 A    3/2015
(Continued)

OTHER PUBLICATIONS

Johansen et al "Sensor Unit for a Surface Plasmon Resonance (SPR) Unit", May 8, 2008, WO2008054282 A1 (Year: 2008).*
(Continued)

*Primary Examiner* — Sang H Nguyen
(74) *Attorney, Agent, or Firm* — Sughrue Mion, PLLC (57) ABSTRACT

The present invention relates to providing a detection device that uses surface plasmon resonance to detect the presence or the amount of a substance to be detected, in which a detection unit can accurately detect scattered light without detecting stray light, and can accurately determine an irradiation angle of excitation light. This detection method uses the detection device that uses surface plasmon resonance to detect the presence or the amount of a substance to be detected. A detection range control unit controls a detection range of a detection unit so that a detection range utilized when the detection unit detects scattered light emitted from a metallic film and front a region on the metallic film differs from a detection range utilized when the detection unit detects fluorescence emitted front a fluorescent substance labeling the substance to be detected winch has been captured by a capturing body.

18 Claims, 9 Drawing Sheets

(56) References Cited

U.S. PATENT DOCUMENTS

| | | |
|---|---|---|
| 10,495,576 B2 | 12/2019 | Matsuo et al. |
| 2006/0066860 A1* | 3/2006 | Sato ................. G01N 21/05 356/445 |
| 2009/0079978 A1 | 3/2009 | Kimura |
| 2013/0175457 A1* | 7/2013 | Wada .................. G01N 21/64 250/234 |
| 2016/0153910 A1* | 6/2016 | Fujii .................. G01N 21/6428 422/69 |
| 2016/0245746 A1 | 8/2016 | Noda et al. |
| 2017/0153182 A1 | 6/2017 | Matsuo et al. |
| 2017/0191125 A1 | 7/2017 | Vijayan et al. |
| 2018/0180545 A1* | 6/2018 | Muramatsu .......... G01N 21/645 |
| 2018/0313756 A1 | 11/2018 | Yamauchi et al. |
| 2020/0271593 A1 | 8/2020 | Noda et al. |
| 2021/0356386 A1 | 11/2021 | Kaneko et al. |

FOREIGN PATENT DOCUMENTS

| | | |
|---|---|---|
| JP | 2018-9802 A | 1/2018 |
| WO | 2015/064704 A1 | 5/2015 |
| WO | 2015/152198 A1 | 10/2015 |
| WO | 2015/182747 A1 | 12/2015 |
| WO | 2017/082089 A1 | 5/2017 |
| WO | 2018/021238 A1 | 2/2018 |
| WO | 2019/064754 A1 | 4/2019 |

OTHER PUBLICATIONS

Matsuo et al "Surface Plasmon Resonance Fluorescence Analysis Method, Surface Plasmon Resonance Fluorescence Analysis Device, and Alignment Method", Oct. 8, 2015, WO2015152198A1 (Year: 2015).*

Nagai et al "Method and Device for Detection", Jan. 8, 2018, JP2018009802A (Year: 2018).*

Extended European Search Report dated Dec. 20, 2022 in European Application No. 20841251.0.

International Search Report dated Jul. 14, 2020 in International Application No. PCT/JP2020/018447.

International Preliminary Report on Patentability with Written Opinion dated Jan. 18, 2022 in International Application No. PCT/JP2020/018447.

* cited by examiner

DETECTION DEVICE AND DETECTION METHOD

CROSS REFERENCE TO RELATED APPLICATIONS

This application is a National Stage of International Application No. PCT/JP2020/018447 filed May 1, 2020, claiming priority based on Japanese Patent Application No. 2019-130432 filed Jul. 12, 2019, the entire disclosures of which are incorporated by reference herein.

TECHNICAL FIELD

The present invention relates to a detection device and a detection method for detecting the presence or amount of a substance to be detected using an enhanced electric field based on surface plasmon resonance (SPR).

BACKGROUND ART

In the measurement for detecting a biological substance such as protein or DNA, if a minute amount of a substance to be detected can be detected with high sensitivity and quantitatively, it is possible to immediately grasp the patient's condition and perform treatment. Therefore, there is a demand for a detection method and a detection device for detecting weak light caused by a trace amount of a substance to be detected with high sensitivity and quantitatively. As one method for detecting a substance to be detected with high sensitivity, the surface plasmon resonance fluorescence analysis method (surface plasmon-field enhanced fluorescent spectroscopy: SPFS) is known (see, for example, WO 2017/082089).

In the SPFS, for example, a prism in which a metal film is disposed on a predetermined surface is used. Then, when the metal film is irradiated with excitation light from the excitation light irradiation unit at an angle at which surface plasmon resonance occurs via the prism, localized field light (enhanced electric field) can be generated on the surface of the metal film. Since the fluorescent substance that labels the substance to be detected captured on the metal film is excited by the localized field light, detecting the fluorescence emitted from the fluorescent substance allows the presence or amount of the substance to be detected to be detected.

Patent Document 1: WO 2017/082089

SUMMARY OT THE INVENTION

Problems to be Solved by the Invention

Figure 1:
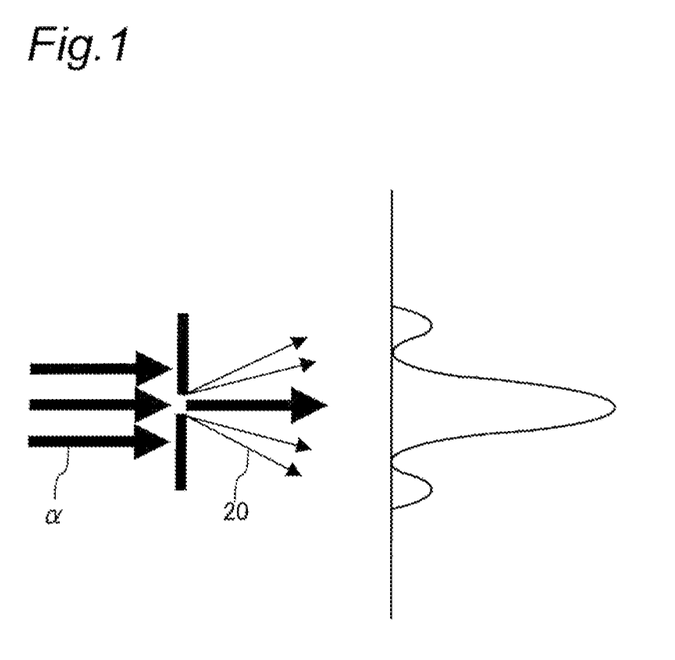
FIG. 1 is a schematic diagram showing a state in which diffracted light is generated when excitation light passes through a slit.

In the SPFS, in order to efficiently excite plasmon resonance, a region corresponding to a region (reaction field) in which a substance to be detected on the metal film is captured is irradiated with excitation light α of substantially parallel light. In addition, in order to reduce the cost of the detection chip, improve the reaction efficiency, and reduce the amount of the specimen to reduce the burden on the subject, the reaction field is set in a limited region, and therefore, after being thinly beam-formed (beam size is reduced) using a pinhole or a slit, the excitation light α is applied to a region corresponding to the reaction field. However, as shown in FIG. 1, thinning the excitation light α generates the diffracted light 20 in the beam passing through the pinhole or the slit, and the peripheral region of the region to be irradiated with the excitation light α of the metal film is irradiated with the diffracted light 20.

Figure 2:
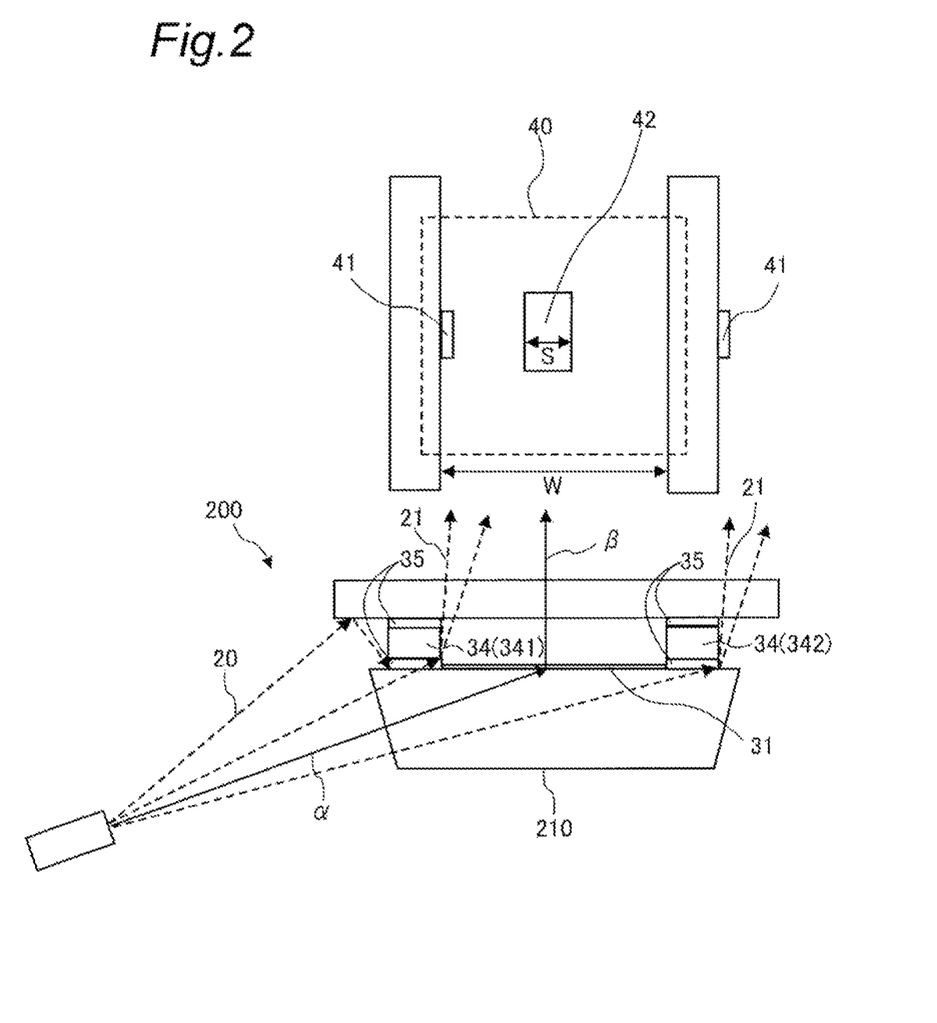
FIG. 2 is a schematic diagram showing a state in which diffracted light becomes stray light.

As shown in FIG. 2, when the diffracted light 20 reaches a structure around the metal film 31 of the detection chip 200, for example, an adhesive layer 35 that adheres the prism 210 and the wall portion 34, the diffracted light 20 is guided through the adhesive layer 35 and scattered to generate stray light 21.

In addition, in the SPFS, in order to generate an enhanced electric field based on plasmon resonance, it is necessary to cause the excitation light α to be incident on the metal film 31 at a predetermined angle. When, in order to adjust the excitation light α to a predetermined incident angle with respect to the metal film 31, the metal film 31 is irradiated with the excitation light α through the prism 210, the plasmon scattered light β having the same wavelength as the excitation light α generated due to the surface plasmon resonance in the metal film 31 may be detected. At this time, when the above-described stray light 21 enters the detection range 40 of the detection unit, as shown in FIG. 2, in addition to the plasmon scattered light β emitted from the region corresponding to the irradiation spot 42 of the excitation light α, the stray light 21 emitted from the stray light occurrence spot 41 is also detected. When not only the plasmon scattered light β but also the stray light 21 is detected as described above, it is difficult to appropriately adjust the incident angle of the excitation light α to an optimum angle (for example, an enhancement angle).

Figure 3A:
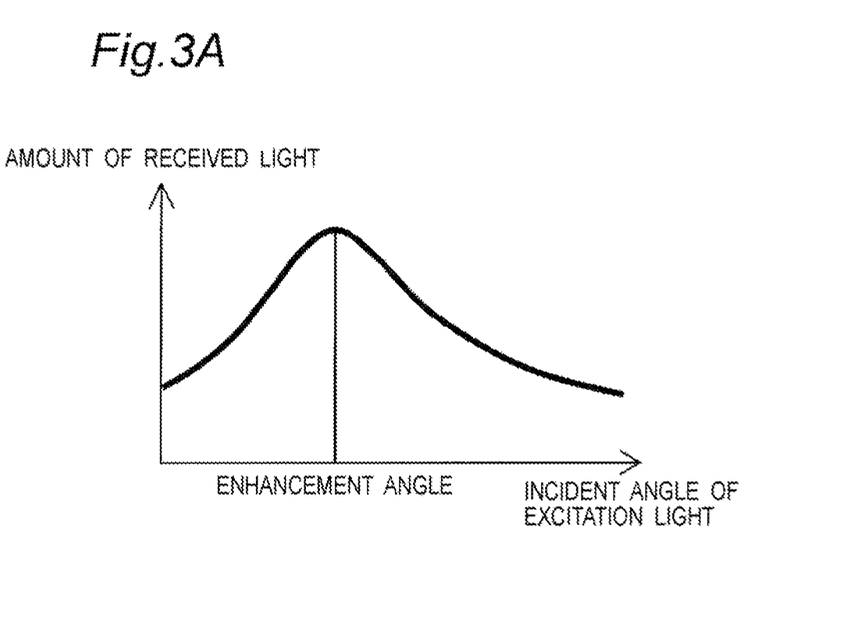
FIG. 3A is a graph showing a relationship between an incident angle of excitation light and an amount of received light of a detection unit when only plasmon scattered light is detected.
Figure 3B:
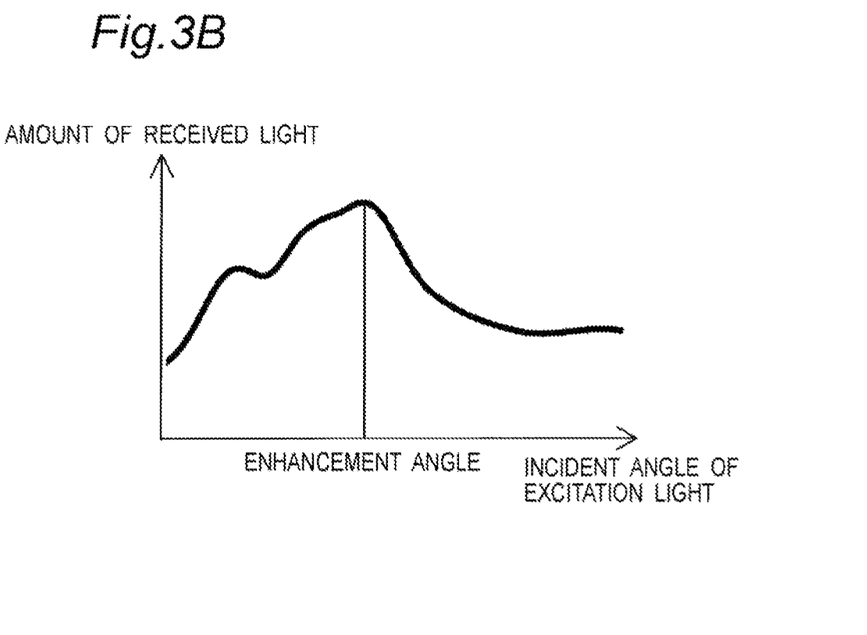
FIG. 3B is a graph showing the relationship between the incident angle of the excitation light and the amount of received light of the detection unit when plasmon scattered light and stray light are detected.

FIG. 3A is a graph showing the relationship between the incident angle of the excitation light α and the amount of received light of the detection unit when only the plasmon scattered light β emitted from the region corresponding to the irradiation spot 42 of the excitation light α is detected, and FIG. 3B is a graph showing the relationship between the incident angle of the excitation light α and the amount of received light of the detection unit when the stray light 21 emitted from the stray light occurrence spot 41 is also detected in addition to the plasmon scattered light β. By scanning the incident angle of the excitation light α, the irradiation position of the diffracted light 20 applied to the metal film 31 is changed, whereby the irregular stray light 21 is detected by the detection unit. Therefore, as is clear from FIGS. 3A and 3B, in a case where the plasmon scattered light β and the stray light 21 are detected, noise occurs in the amount of received light, and it may be difficult to detect a peak. Therefore, when stray light is also detected, the plasmon scattered light β cannot be accurately detected, and the incident angle (for example, the enhancement angle) of the excitation light α cannot be accurately determined.

Here, in order for the detection unit not to detect stray light, it is conceivable to sufficiently separate a structure (for example, adhesive layer 35) that causes stray light from the detection range 40 of the detection unit, for example, to make a detection chip larger. However, in this case, the cost increases due to the increase in the size of detection chip, the burden on the subject increases due to the need to increase the specimen amount, and the reaction efficiency of the reaction field decreases due to the increase in the flow path width. In addition, the detection unit may receive a large amount of autofluorescence generated from the prism 210, and the measurement performance may be deteriorated. Therefore, it is not easy to largely separate the structure from the detection range 40 of the detection unit.

The present invention has been made in view of the above circumstances, and has an object to provide, in a detection device and a detection method for detecting the presence or amount of a substance to be detected using an enhanced electric field based on surface plasmon resonance, a detection device and a detection method which does not increase the cost of the detection chip, which does not deteriorate the measurement performance of the substance to be detected, and which includes a detection unit capable of accurately detecting plasmon scattered light β without detecting stray light derived from excitation light and accurately determining an incident angle of the excitation light.

Means for Solving the Problems

A detection device according to an embodiment of the present invention is a detection device configured to detect presence or an amount of a substance to be detected using an enhanced electric field based on surface plasmon resonance, the detection device including: a chip holder configured to hold a detection chip including a prism having an incident surface and a film formation surface, a metal film disposed on the film formation surface, and a capturing body fixed on the metal film and configured to capture a substance to be detected; a light source configured to irradiate the metal film of the detection chip held by the chip holder with excitation light through the prism; a detection unit arranged to face the metal film of the detection chip held by the chip holder, the detection unit configured to detect light emitted from the metal film and a region on the metal film when the light source irradiates the metal film with the excitation light; and a detection range control unit configured to control a detection range of the detection unit in the metal film and the region on the metal film. The detection range control unit controls a detection range of the detection unit so that a detection range when the detection unit detects plasmon scattered light β emitted from the metal film and the region on the metal film is different from a detection range when the detection unit detects fluorescence emitted from a fluorescent substance that labels the substance to be detected captured by the capturing body.

A detection method according to an embodiment of the present invention is a detection method for detecting presence or an amount of a substance to be detected using an enhanced electric field based on surface plasmon resonance, the detection method including: preparing a detection chip including: a prism having an incident surface and a film formation surface, a metal film disposed on the film formation surface, and a capturing body fixed on the metal film and configured to capture a substance to be detected; irradiating the metal film with excitation light through the prism and detecting plasmon scattered light β emitted from the metal film and a region on the metal film; and irradiating the metal film with the excitation light through the prism and detecting fluorescence emitted from a fluorescent substance that labels the substance to be detected captured by the capturing body. A detection range of the plasmon scattered light β when the plasmon scattered light β is detected is different from a detection range of the fluorescence when the fluorescence is detected.

Effect of the Invention

According to the present invention, in the detection device and the detection method for detecting the presence or the amount of the substance to be detected using the enhanced electric field based on the surface plasmon resonance, the plasmon scattered light β can be accurately detected without the detection unit detecting stray light derived from the excitation light, and the incident angle of the excitation light can be accurately determined.

MODES FOR CARRYING OUT THE INVENTION

Hereinafter, embodiments of the present invention will be described in detail with reference to the drawings.

First Embodiment (Configuration of Detection Device)

Figure 4:
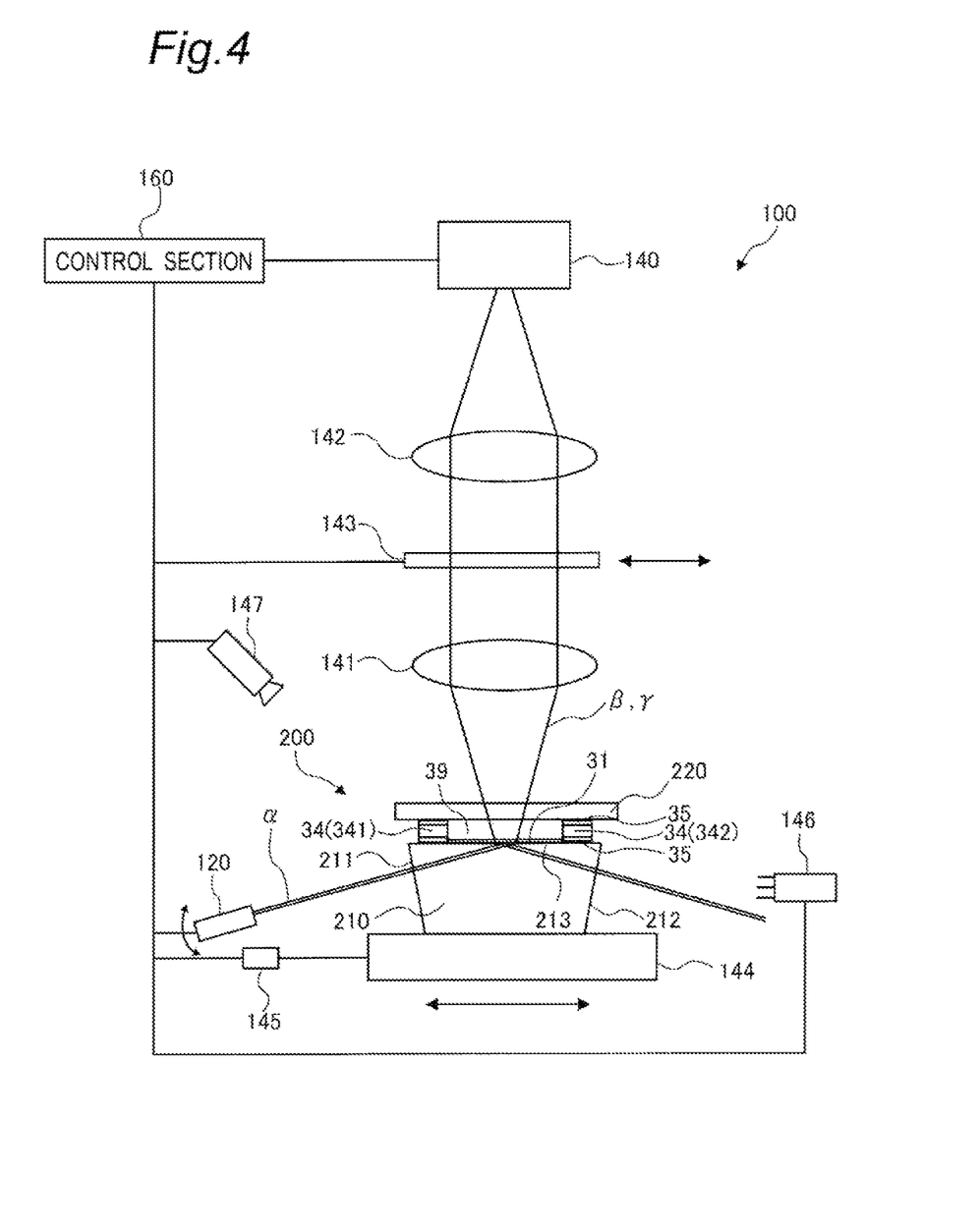
FIG. 4 is a schematic diagram showing a detection device according to a first embodiment of the present invention.

FIG. 4 is a diagram showing a detection device 100 according to the first embodiment of the present invention.

The detection device 100 includes: a light source 120 for irradiating the detection chip 200 with the excitation light α, a first lens 141, a second lens 142, an excitation light cut filter 143, a detection unit 140 for detecting light (plasmon scattered light β or fluorescence γ) emitted from the detection chip 200, a chip holder 144, a chip holder moving means 145, and a control unit 160. The detection device 100 is used together with the detection chip 200. Thus, the detection chip 200 will be described first, and then each component of the detection device 100 will be described.

As shown in FIG. 4, the detection chip 200 includes a prism 210 having an incident surface 211, a film formation surface 213, and an emitting surface 212, a metal film 31 disposed on the film formation surface 213 of the prism 210, and a flow path lid 220 disposed on the metal film 31.

The prism 210 is made of a member transparent to the excitation light α. The prism 210 has an incident surface 211, a film formation surface 213 on which a metal film 31 is formed, and an emitting surface 212. The incident surface 211 allows the excitation light α from the light source 120 to be incident on the inside of the prism 210. A metal film 31 is formed on the film formation surface 213. The excitation light α incident on the inside of the prism 210 is reflected by the metal film 31. More specifically, the excitation light α is reflected at the interface (film formation surface 213) between the prism 210 and the metal film 31. The emitting surface 212 emits the excitation light α reflected by the metal film 31 to outside the prism 210. The shape of the prism 210 is not particularly limited. In the present exemplary embodiment, the shape of the prism 210 is a column body having a trapezoidal bottom. A surface corresponding to one base of the trapezoid is the film formation surface 213, a surface corresponding to one leg is the incident surface 211, and a surface corresponding to the other leg is the emitting surface 212. The trapezoid serving as the bottom surface is preferably a substantially isosceles trapezoid. Thus, the incident surface 211 and the emitting surface 212 are substantially symmetrical, and the S-polarized component of the excitation light α is less likely to stay by being totally reflected in the prism 210. It should be noted that since only the P-polarized component of the excitation light contributes to plasmon resonance, the S-polarized component is reflected by the metal film 31. In addition, the incident surface 211 is formed so that the excitation light α does not return to the light source 120. This is because, if the excitation light α returns to the light source 120 being a laser diode, for example, the excited state of the laser diode is disturbed, and the wavelength and power of the excitation light α fluctuate. Therefore, the angle of the incident surface 211 is set so that the excitation light α is not perpendicularly incident on the incident surface 211 in the scanning range centered on the ideal enhancement angle. For example, the angle between the incident surface 211 and the film formation surface 213 and the angle between the film formation surface 213 and the emitting surface 212 are both about 80°. Examples of the material of the prism 210 include resin and glass. The material of the prism 210 is preferably a resin having a refractive index of 1.4 to 1.6 and small birefringence.

The metal film 31 is formed on the film formation surface 213 of the prism 210. Providing the metal film 31 allows interactions between photons of the excitation light α incident on the film formation surface 213 under a total reflection condition and free electrons in the metal film 31 (surface plasmon resonance; SPR) to occur, and an enhanced electric field (localized field light) to be generated on the surface of the metal film 31. The material of the metal film 31 is not particularly limited as long as it is a metal that causes surface plasmon resonance. Examples of the material of the metal film 31 include gold, silver, copper, aluminum, and alloys thereof. Among them, the metal constituting the metal film 31 is preferably gold from the viewpoint of suppressing non-specific adsorption of a substance in a specimen. In the present embodiment, a metal constituting the metal film 31 is gold. A method for forming the metal film 31 is not particularly limited. Examples of the method for forming the metal film 31 include sputtering, vapor deposition, and plating. The thickness of the metal film 31 is not particularly limited, but is preferably within the range of 30 to 70 nm.

In addition, although not particularly shown, a capturing body for capturing a substance to be detected is immobilized on a surface of the metal film 31 not facing the prism 210. By immobilizing the capturing body, the substance to be detected can be selectively detected. In the present embodiment, the capturing body is uniformly immobilized in a predetermined region on the metal film 31. The kind of the capturing body is not particularly limited as long as the capturing body can capture the substance to be detected. For example, the capturing body is an antibody specific to the substance to be detected or a fragment thereof.

The flow path lid 220 is disposed on a surface not facing the prism 210 of the metal film 31 across the flow path 39. In the present embodiment, the flow path lid 220 is joined to the film formation surface 213 or the metal film 31 via the wall portion 34 and the adhesive layer 35. The wall portion 34 defines a storage portion for storing liquid on the metal film 31. In the present embodiment, the storage portion is the flow path 39, but may be a well. In the present embodiment, the wall portion 34 includes at least a first side wall 341 and a second side wall 342 facing each other, and the second side wall 342 is farther away from the light source 120 than the first side wall 341. It should be noted that in the present embodiment, the wall portion 34 has a light shielding function, but the adhesive layer 35 does not have a light shielding function. Specifically, the flow path lid 220 is joined to the metal film 31 or the prism 210 by, for example, adhesion with a double-sided tape or an adhesive, laser welding, ultrasonic welding, pressure bonding using a clamp member, or the like.

When the metal film 31 is formed only on a part of the film formation surface 213 of the prism 210, the flow path lid 220 may be disposed on the film formation surface 213 across the flow path 39. The flow path lid 220 forms, together with the metal film 31, the wall portion 34, and the adhesive layer 35, a flow path 39 through which liquids such as a specimen, a fluorescent labeling liquid, and a cleaning liquid flow. The capture substance is exposed in the flow path 39. Each of both ends of the flow path 39 is connected to an injection port and a discharge port (both are not shown) formed on the upper surface of the flow path lid 220. When the liquids are injected into the flow path 39, these liquids come into contact with the capture substance in the flow path 39.

The flow path lid 220 is made of a material transparent to light (plasmon scattered light β and fluorescence γ) emitted from a surface not facing the prism 210 of the metal film 31 and its vicinity. Examples of the material of the flow path lid 220 include resin. If these rays of light can be guided to the detection unit 140, a part of the flow path lid 220 may be made of an opaque material.

As shown in FIG. 4, the excitation light α guided to the prism 210 enters the prism 210 from the incident surface 211. The excitation light α incident into the prism 210 is incident on the interface (film formation surface 213) between the prism 210 and the metal film 31 so as to have a total reflection angle (angle at which surface plasmon resonance occurs). The reflected light from the interface is emitted from the emitting surface 212 to outside the prism 210. On the other hand, incidence of the excitation light α on the interface at an angle at which the surface plasmon resonance occurs emits the plasmon scattered light R and/or the fluorescence γ from the metal film 31 and the vicinity thereof toward the detection unit 140.

Next, each component of the detection device 100 will be described. As described above, the detection device 100 includes the light source 120, the first lens 141, the second lens 142, the excitation light cut filter 143, the detection unit 140, the chip holder 144, the chip holder moving means 145, and the control unit 160.

The light source 120 emits the excitation light α. The position and orientation of the light source 120 are adjusted by the control unit 160. Thus, the incident angle of the excitation light α with respect to the interface (film formation surface 213) between the prism 210 and the metal film 31 is adjusted. When the metal film 31 is irradiated with the excitation light α, the plasmon scattered light β having the same wavelength as the excitation light α, the fluorescence γ emitted from the fluorescent substance, and the like are emitted upward from the surface not facing the prism 210 of the metal film 31 and the vicinity thereof. In addition, the excitation light α is reflected by the interface between the prism 210 and the metal film 31, and is emitted from the emitting surface 212 to outside the prism 210.

In the present embodiment, the light source 120 is a laser diode (hereinafter abbreviated as "LD"), and emits excitation light α (single mode laser light) toward the incident surface 211 of the detection chip 200. More specifically, the light source 120 emits only the P waves with respect to the interface toward the incident surface 211 so that the excitation light α has a total reflection angle with respect to the interface (film formation surface 213) between the prism 210 and the metal film 31 of the detection chip 200. The excitation light α is preferably substantially parallel light.

It should be noted that the type of the light source 120 is not particularly limited, and does not need to be an LD. Examples of the light source 120 include a light emitting diode, a mercury lamp, and other laser light sources. When the light emitted from the light source 120 is not a beam, the light emitted from the light source 120 is preferably converted into a beam by a lens, a mirror, a pinhole, a slit, or the like. In the present embodiment, the beam size of the light emitted from the light source 120 is controlled by the slit. The beam size of the excitation light α is preferably controlled to 0.5 to 2.0 mm on the metal film surface. In addition, When the light emitted from the light source 120 is not monochromatic light, the light emitted from the light source 120 is preferably converted into monochromatic light by a diffraction grating or the like. Furthermore, when the light emitted from the light source 120 is not linearly polarized light, the light emitted from the light source 120 is preferably converted into linearly polarized light by a polarizer or the like.

The first lens 141 forms an image of the plasmon scattered light β or the fluorescence γ emitted from on the metal film 31 on the light receiving unit of the detection unit 140. The first lens 141 is, for example, a condenser lens, and condenses light emitted from the metal film 31. The second lens 142 is, for example, an image forming lens, and forms an image of the light condensed by the first lens 141 on the light receiving unit of the detection unit 140. The optical paths between the two lenses are substantially parallel optical paths.

The excitation light cut filter 143 blocks the plasmon scattered light β, stray light derived from the excitation light α, and the like, and transmits the fluorescence γ, thereby preventing light other than the wavelength of the fluorescence γ from reaching the detection unit 140. That is, the excitation light cut filter 143 removes a noise component from the light emitted from the metal film 31, and enables the detection unit 140 to detect the fluorescence γ at a high S/N ratio. In FIG. 4 showing the present embodiment, the excitation light cut filter 143 is disposed between the first lens 141 and the second lens 142, but when the enhancement angle is determined, the excitation light cut filter 143 is removed from the optical path so that the plasmon scattered light β can be detected.

The detection unit 140 is disposed so as to face a surface not facing the prism 210 of the metal film 31 of the detection chip 200. The detection unit 140 receives light (plasmon scattered light β or fluorescence γ) emitted from on the metal film 31. The light receiving unit of the detection unit 140 includes, for example, an image sensor, a photomultiplier tube, a photodiode, or the like. The first lens 141, the excitation light cut filter 143, the second lens 142, and the detection unit 140 are arranged in this order from the metal film 31 side so as to face the surface of the metal film 31.

The detection chip 200 is set on the chip holder 144. The chip holder 144 is not particularly limited as long as the detection chip 200 can be set. The chip holder 144 has a shape that can set the detection chip 200 and does not hinder the optical path of the excitation light α, the reflected light, the fluorescence γ, and the like. For example, the chip holder 144 is provided with an opening through which these rays of light pass.

The chip holder moving means 145 moves the chip holder 144. The chip holder moving means 145 moves, for example, the chip holder 144 in one direction and the opposite direction. The chip holder moving means 145 is, for example, a motor or the like.

The control unit 160 centrally controls the light source 120, the excitation light cut filter 143, the detection unit 140, and the chip holder moving means 145. Specifically, the control unit 160 controls the position and orientation of the light source 120, and sets the incident angle of the excitation light α with respect to the metal film 31 to a predetermined angle. In addition, when determining the enhancement angle, the control unit 160 removes the excitation light cut filter 143 from on the optical path so that the plasmon scattered light β reaches the detection unit 140. In addition, when receiving the fluorescence γ, the control unit 160 disposes the excitation light cut filter 143 on the optical path so that light having the same wavelength as the excitation light α (plasmon scattered light β, stray light derived from the excitation light α, or the like) does not reach the detection unit 140. In addition, the control unit (detection range control unit) 160 controls the chip holder moving means 145 to move the chip holder 144 and change the detection range of the detection unit 140. The control unit 160 is, for example, a computer that executes software.

The detection device 100 may include a shape information acquisition unit 146 that acquires shape information on the detection chip 200. The control unit (detection range control unit) 160 can determine the detection range 40 when the detection unit 140 detects the plasmon scattered light β based on the shape information on the detection chip 200 acquired by the shape information acquisition unit 146.

The above-described shape information on the detection chip is, for example, information indicating a positional relationship between the prism 210 and the first side wall 341. For example, at the time of manufacturing the detection chip 200, this positional relationship can be put in a barcode or the like attached to the detection chip 200. The shape information acquisition unit 146 is, for example, a barcode reader, and can acquire the shape information by reading the barcode. Based on the acquired shape information, the control unit (detection range control unit) 160 can determine the detection range 40 of the detection unit 140. Thus, stray light can be removed without being affected by the manufacturing variations of the detection chip 200, and the enhancement angle can be accurately measured.

The detection device 100 may include a positional information detection unit 147 that detects positional information of the detection chip 200. The positional information of the detection chip 200 may be information including the position of at least one of the first side wall 341 and the second side wall 342 of the detection chip 200. The positional information detection unit 147 is, for example, a camera, and can acquire positional information on at least one of the first side wall 341 and the second side wall 342 using the camera. Based on the acquired positional information on the detection chip, the control unit (detection range control unit) 160 can determine the detection range 40 of the detection unit 140 necessary for stray light removal.

(Operation of Detection Device)

Figure 5:
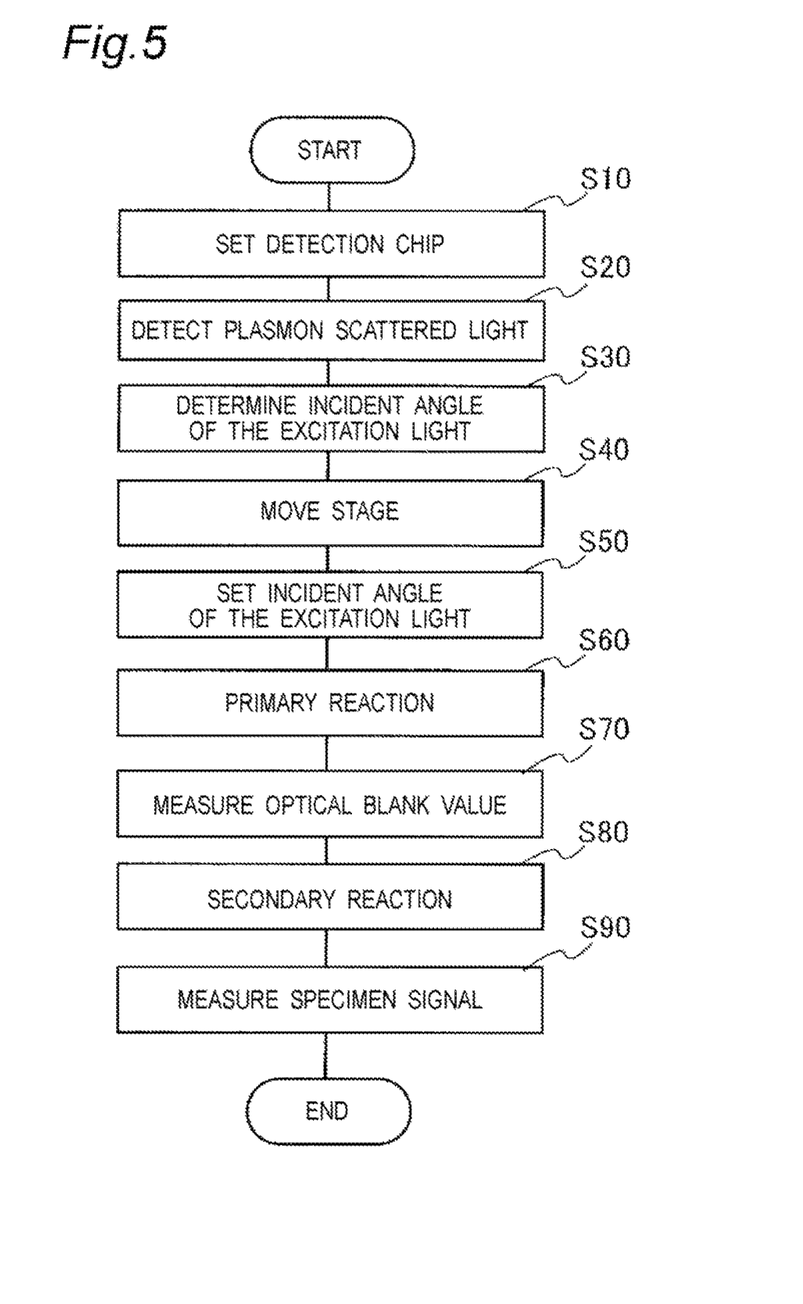
FIG. 5 is a flowchart showing a detection method according to an embodiment of the present invention.

FIG. 5 is a flowchart showing a detection method according to an embodiment of the present invention using the detection device 100.

First, preparation for measurement is made. Specifically, the detection chip 200 is set in the chip holder 144 of the detection device 100 (step S10). In addition, when a humectant is present in the flow path 39 of the detection chip 200, the inside of the flow path 39 is cleaned to remove the humectant so that the capture substance can appropriately capture the substance to be detected.

Figure 6A:
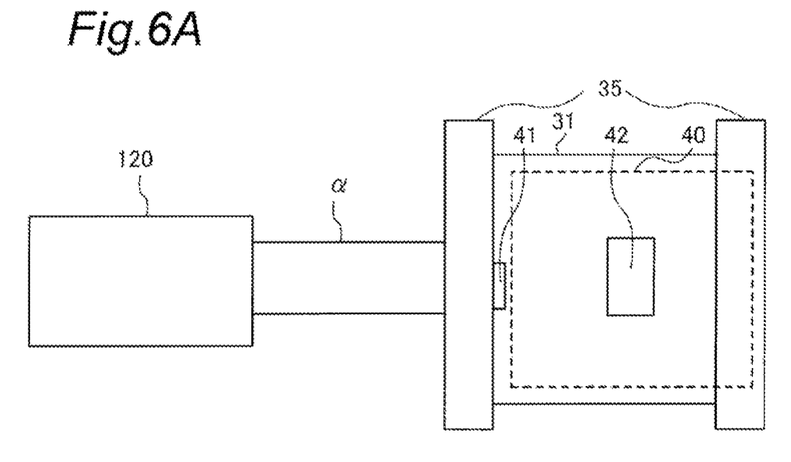
FIG. 6A is a schematic diagram showing a light receiving range of a detection unit and a position of a light source when an incident angle of excitation light is determined in a detection device.

Next, the plasmon scattered light β is detected (step S20). Specifically, the chip holder 144 is moved from the position where the detection chip 200 is set so that a predetermined position of the metal film 31 (film formation surface 213) can be irradiated with the excitation light α. The incident angle of the excitation light α with respect to the metal film 31 (film formation surface 213) is scanned while a predetermined position of the metal film 31 (film formation surface 213) is irradiated with the excitation light α, the plasmon scattered light β is detected with the detection unit 140, and the optimum incident angle (enhancement angle) of the excitation light α for generating an enhanced electric field based on plasmon resonance is determined (step S30). This is performed by the control unit 160 controlling the light source 120 to scan the incident angle of the excitation light α with respect to the metal film 31 (film formation surface 213) while irradiating a predetermined position of the metal film 31 (film formation surface 213) with the excitation light α. At this time, as shown in FIG. 6A described below, the control unit 160 moves the chip holder 144 so that the end portion of the first side wall 341 on a side of the storage portion does not enter the detection range 40 of the detection unit 140. When the end portion of the first side wall 341 on the side of the storage portion enters the detection range 40, the control unit 160 controls the chip holder moving means 145 to move the chip holder 144 so that the end portion of the first side wall 341 does not enter the detection range 40. In addition, the control unit 160 controls the excitation light cut filter 143 so that the excitation light cut filter 143 is not present on the optical path, and controls the detection unit 140 so that the detection unit 140 detects the plasmon scattered light β from on the metal film 31 (the surface of the metal film 31 and the vicinity thereof). The plasmon scattered light s from the on metal film 31 (the surface of the metal film 31 and the vicinity thereof) reaches the detection unit 140 via the first lens 141 and the second lens 142.

FIG. 6A is a schematic diagram showing the detection range 40 of the detection unit 140 and the position of the light source 120 when the optimum incident angle (enhancement angle) of the excitation light α is determined. In this figure, a state when the detection chip 200 and the light source 120 are viewed from the detection unit 140 side is shown. As shown in FIGS. 6A and 2, the stray light derived from the excitation light α is guided toward the traveling direction side of the excitation light α through the adhesive layer 35 positioned on the first side wall 341 on the light source 120 side, and enters the flow path 39 from the end portion of the adhesive layer 35. That is, the stray light occurrence spot 41 is likely to occur at the end portion of the first side wall 341 on the side of the storage portion, and large stray light is generated. However, in the present embodiment, when plasmon scattered light is detected, the detection chip 200 (chip holder 144) is moved so that the end portion of the first side wall 341 on the side of the storage portion does not enter the detection range 40 of the detection unit 140 and the region corresponding to the irradiation spot 42 of the excitation light α enters the detection range 40 of the detection unit 140. Therefore, the stray light occurrence spot 41 does not fall within the detection range 40, but the irradiation spot 42 of the excitation light α falls within the detection range 40. Therefore, the control unit 160 can obtain accurate data on the relationship between the incident angle of the excitation light α and the intensity of the plasmon scattered light β while preventing the influence of stray light derived from the excitation light α.

In addition, as shown in FIG. 2, since the stray light occurrence spot 41 may also occur at the end portion of the second side wall 342 on a side opposite to the storage portion, it is more preferable that the end portion does not fall within the detection range 40.

It should be noted that regarding the facing direction between the first side wall 341 and the second side wall 342, the ratio (S/W) of the length (S) of the irradiation spot of the excitation light on the metal film 31 to the distance (W) between the first side wall 341 and the second side wall 342 is preferably more than $0.1$ and less than 0.5, and more preferably more than 0.2 and less than 0.4.

As described above, when the ratio (S/W) exceeds 0.1, the size of the irradiation spot 42 of the excitation light α becomes an appropriate size, and the light amount of the fluorescence caused by the amount of the substance to be detected becomes a sufficient amount, so that the detection accuracy of the substance to be detected becomes favorable. More specifically, the substance to be detected is captured in the reaction field (region where the capturing body is immobilized) in the flow path. When the size of the irradiation spot 42 of the excitation light α is appropriate for the reaction field, a fluorescent substance for labeling the captured substance to be detected can be appropriately excited, and the light amount of fluorescence sufficient for securing detection accuracy can be obtained.

As described above, when the ratio (S/W) is less than 0.5, the irradiation spot of the excitation light and the place where the stray light occurs can be sufficiently separated from each other, and the operation for excluding the place where the stray light occurs from the detection range 40 becomes easy.

Then, the control unit 160 analyzes the data and determines the incident angle (enhancement angle) of the excitation light at which the intensity of the plasmon scattered light β is maximized. It should be noted that the enhancement angle is basically determined by the material and shape of the prism 210, the thickness of the metal film 31, the refractive index of the liquid in the flow path 39, and the like, but slightly fluctuates due to various factors such as the type and amount of the substance in the flow path 39, and the shape error of the prism 210. Therefore, it is preferable to determine the enhancement angle each time detection is performed. The enhancement angle is determined on the order of about 0.1°.

Next, the chip holder 144 is moved (step S40). Specifically, the control unit 160 controls the chip holder moving means 145 to cause the chip holder moving means 145 to move the chip holder 144, so that the irradiation spot 42 of the excitation light α is positioned near the center of the detection range 40 as shown in FIG. 6B.

Figure 6B:
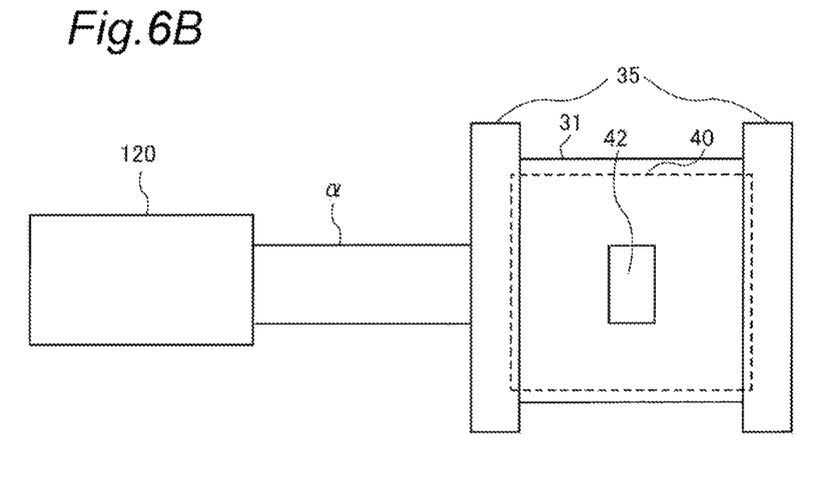
FIG. 6B is a schematic diagram showing a light receiving range of a detection unit and a position of a light source when a substance to be detected is detected in the detection device.

As shown in FIG. 6B, the end portion of the first side wall 341 on the side of the storage portion falls within the detection range 40, and the stray light occurring here has the same wavelength as the excitation light α. As will be described below, in the measurement of the optical blank value and the measurement of the specimen signal, since the excitation light cut filter 143 is inserted to measure the signal, the stray light 21 having the same wavelength as the excitation light α is not detected by the detection unit 140 and does not affect the measurement performance. Furthermore, by moving the detection range so that the irradiation spot 42 of the excitation light α falls within the vicinity of the center of the detection range 40, even if the positional relationship between the irradiation spot 42 of the excitation light α and the detection range 40 varies due to setting variations of the detection chip or the like, the fluorescence from the reaction field (region where the capturing body is immobilized) on the metal film 31 can be efficiently and reproducibly detected without the irradiation spot 42 of the excitation light α falling outside the detection range, and the detection accuracy (accuracy, accuracy of absolute value) of the substance to be detected can be improved.

Here, comparing FIG. 6A with FIG. 6B, the detection range 40 of the detection unit 140 when the detection unit 140 detects scattered light may be farther from the light source 120 than the detection range 40 of the detection unit 140 when the detection unit 140 detects fluorescence. In addition, the irradiation spot 42 (irradiation position of excitation light) of the excitation light α on the metal film 31 when the detection unit 140 detects plasmon scattered light (β may be farther from the light source 120 than the irradiation spot 42 (irradiation position of excitation light) (see FIG. 6B) of the excitation light α on the metal film 31 when the detection unit 140 detects fluorescence.

It should be noted that, in steps S20 and S40, moving the chip holder 144 relatively moves the position of the detection range 40 of the detection unit 140 with respect to the detection chip 200, but moving the detection unit 140 may relatively move the detection range 40 of the detection unit 140 with respect to the detection chip 200.

Figure 7:
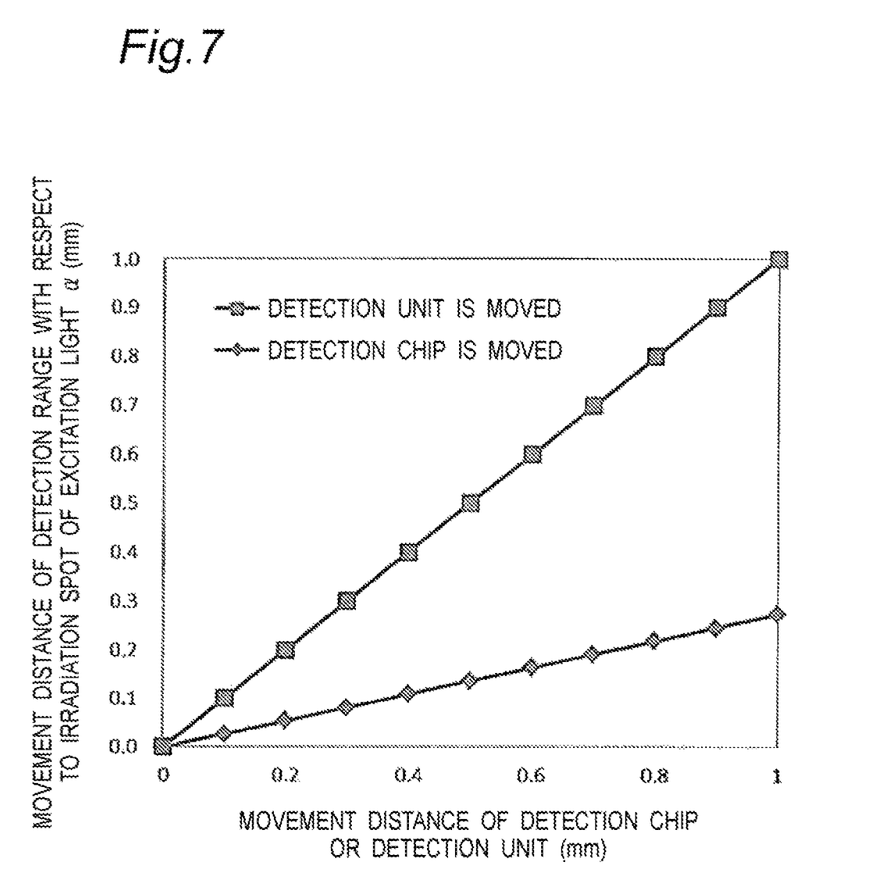
FIG. 7 is a graph showing a relative movement distance of a detection range of a detection unit with respect to an irradiation spot of excitation light when a detection chip is moved and when a detection unit is moved.

FIG. 7 is a graph showing a relative movement distance of the detection range 40 of the detection unit 140 with respect to the irradiation spot 42 of the excitation light α when the detection chip 200 is moved and when the detection unit 140 is moved. When the detection unit 140 is moved without the chip holder 144 (detection chip 200) being moved, the position of the irradiation spot of the excitation light α does not change, but the position of the detection range 40 of the detection unit 140 is moved by the amount of movement of the detection unit 140. Therefore, the relative movement distance of the detection range 40 of the detection unit 140 with respect to the irradiation spot of the excitation light α becomes longer by the same distance as the movement distance of the detection unit 140. On the other hand, when the chip holder 144 (detection chip 200) is moved without the detection unit 140 being moved, the position of the detection range 40 of the detection unit 140 is moved by the amount of movement of the chip holder 144 (detection chip 200), but the position of the irradiation spot of the excitation light α is also moved. Therefore, the relative movement distance of the detection range 40 of the detection unit 140 with respect to the irradiation spot of the excitation light α is shorter than the distance by which the chip holder 144 (detection chip 200) is moved. As described above, when the chip holder 144 (detection chip 200) is moved, the relative position of the detection range 40 of the detection unit 140 with respect to the irradiation spot of the excitation light α is less likely to change, which is preferable from the viewpoint of the detection accuracy.

Next, the incident angle of the excitation light α with respect to the metal film 31 (film formation surface 213) is set to the enhancement angle determined in step S30 (step S50). Specifically, the control unit 160 controls the light source 120 to set the incident angle of the excitation light α with respect to the metal film 31 (film formation surface 213) to the enhancement angle. In the subsequent steps, the incident angle of the excitation light α with respect to the metal film 31 (film formation surface 213) remains at the enhancement angle.

Next, the substance to be detected in the specimen is reacted with the capture substance (primary reaction, step S60). Specifically, the specimen is injected into the flow path 39, and the specimen and the capture substance are brought into contact with each other. When the substance to be detected is present in the specimen, at least a part of the substance to be detected is captured by the capture substance. Thereafter, the inside of the flow path 39 is cleaned with a buffer solution or the like to remove a substance not captured by the capture substance. The type of specimen is not particularly limited. Examples of the specimen include body fluids such as blood, serum, plasma, urine, nasal fluid, saliva, and semen, and diluents thereof.

Next, an optical blank value is measured (step S70). Specifically, the control unit 160 controls the light source 120 so that the light source 120 emits the excitation light α. At the same time, the control unit 160 controls the detection unit 140 so that the detection unit 140 detects light having the same wavelength as fluorescence γ. In addition, at this time, the control unit 160 moves the excitation light cut filter 143 so that the excitation light cut filter 143 is present on the optical path. Thus, since the excitation light cut filter 143 does not transmit the plasmon scattered light β and the stray light derived from the excitation light α, only light having the same wavelength as the fluorescence γ is detected by the detection unit 140. The obtained detection value is recorded as an optical blank value.

Next, the substance to be detected captured by the capture substance is labeled with a fluorescent substance (secondary reaction, step S80). Specifically, a fluorescent labeling liquid is injected into the flow path 39. The fluorescent labeling liquid is, for example, a buffer solution containing an antibody (secondary antibody) labeled with a fluorescent substance. When the fluorescent labeling liquid is injected into the flow path 39, the fluorescent labeling liquid comes into contact with the substance to be detected, and the substance to be detected is labeled with the fluorescent substance. Thereafter, the inside of the flow path 39 is cleaned with a buffer solution or the like and free fluorescent substances and the like are removed.

Next, the metal film 31 (film formation surface 213) is irradiated with the excitation light α, and fluorescence γ emitted from the fluorescent substance on the metal film 31 (the surface of the metal film 31 and the vicinity thereof) is detected (specimen signal measurement, step S90). Specifically, the control unit 160 controls the light source 120 so that the light source 120 emits the excitation light α. At the same time, the control unit 160 controls the detection unit 140 so that the detection unit 140 detects fluorescence γ emitted from on the metal film 31 (metal film 31 and its vicinity). In addition, also at this time, the control unit 160 moves the excitation light cut filter 143 so that the excitation light cut filter 143 is present on the optical path. Thus, since the excitation light cut filter 143 does not transmit the plasmon scattered light β and the stray light derived from the excitation light α, only the fluorescence ν is detected by the detection unit 140.

Next, the control unit 160 subtracts the optical blank value detected in step S70 from the obtained detection value (signal value) to calculate a difference signal value corresponding to the amount of the substance to be detected. From this difference signal value, information on the presence or absence or amount of the substance to be detected in the specimen can be obtained.

It should be noted that when the detection device 100 includes the shape information acquisition unit 146, a step of acquiring the shape information on the detection chip 200 may be performed between step S10 and step S20. In this case, the control unit (detection range control unit) 160 determines the detection range of the detection unit 140 when the detection unit 140 detects the plasmon scattered light β based on the acquired shape information on the detection chip 200.

In addition, when the detection device 100 includes the positional information detection unit 147, a step of detecting the positional information on the detection chip may be performed between step S10 and step S20. In this case, the control unit (detection range control unit) 160 determines the detection range of the detection unit 140 when the detection unit 140 detects the plasmon scattered light β based on the acquired positional information on the detection chip 200.

(Effect)

In the detection device and the detection method according to the present embodiment, the position of the light receiving range is different between the light receiving range at the time of detecting the plasmon scattered light β in order to determine the enhancement angle and the light receiving range at the time of detecting the fluorescence in order to detect the presence or the amount of the substance to be detected. Thus, when the plasmon scattered light β is detected in order to determine the enhancement angle, stray light derived from (diffracted light of) the excitation light is less likely to fall within the light receiving range of the detection unit, and the enhancement angle can be accurately determined. In addition, when the presence or the amount of the substance to be detected is detected, the maximum amount of fluorescence can be received, and the detection accuracy of the substance to be detected is improved.

Second Embodiment (Configuration of Detection Device)

Figure 8:
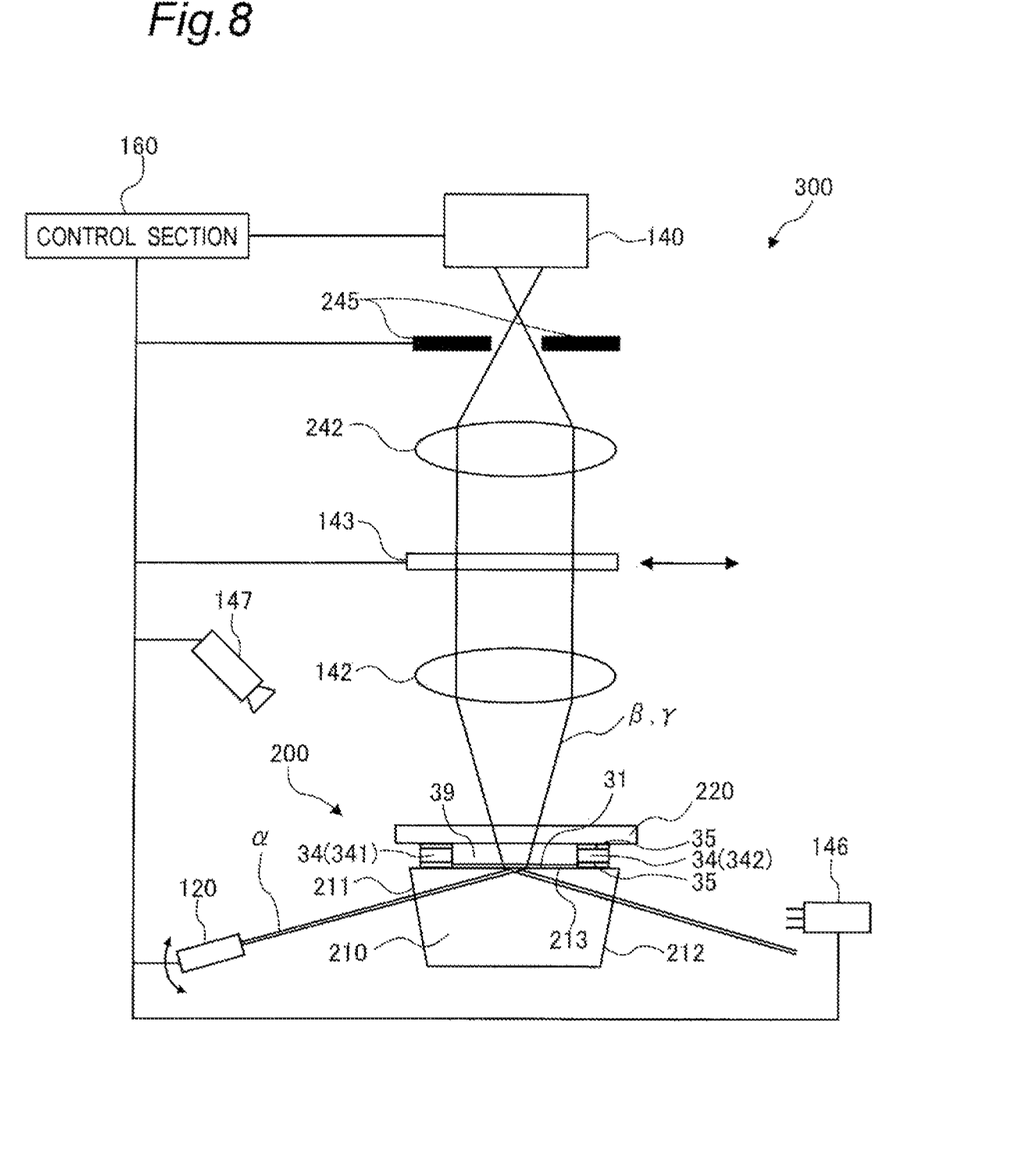
FIG. 8 is a schematic diagram showing a detection device according to a second embodiment of the present invention.

FIG. 8 is a diagram showing a detection device 300 according to the second embodiment of the present invention. Means for changing the light receiving range 40 of the detection unit 140 is different between the detection device 100 according to the first embodiment and the detection device 300 according to the second embodiment. Regarding the detection device 300, the same components as those of the detection device 100 are denoted by the same reference numerals, and the description thereof will be omitted.

In the present embodiment, the detection device 300 further includes a diaphragm 245 arranged between the detection chip 200 and the detection unit 140. The diaphragm 245 adjusts the detection range 40 when the detection unit 140 detects light emitted from the metal film 31 and the region on the metal film 31. Specifically, under the control of the control unit (detection range control unit) 160, the diaphragm 245 narrows the light receiving range of the detection unit 140 when the detection unit 140 detects the plasmon scattered light β in order to determine the enhancement angle, and widens the light receiving range of the detection unit 140 when the detection unit 140 detects fluorescence in order to detect the presence or amount of the substance to be detected. In the present embodiment, the diaphragm 245 is disposed between the second lens 242 and the detection unit 140, but the position of the diaphragm 245 is not particularly limited as long as the diaphragm 245 can exhibit the above function. In particular, the surface of the diaphragm 245 and the surface of the metal film 31 are desirably optically conjugated surfaces.

(Operation of Detection Device)

Figure 9A:
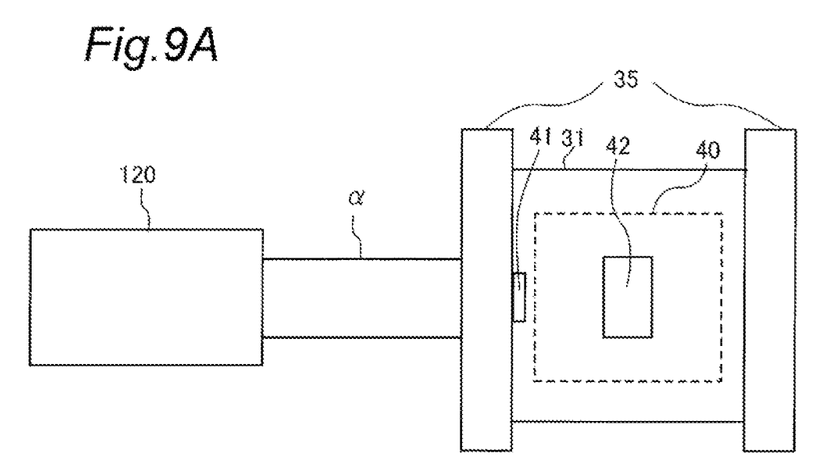
FIG. 9A is a schematic diagram showing a light receiving range of a detection unit and a position of a light source when an incident angle of excitation light is determined in a detection device according to the second embodiment.

FIG. 9A is a schematic diagram showing the detection range 40 of the detection unit 140 and the position of the light source 120 when the optimum incident angle (enhancement angle) of the excitation light α is determined. In this figure, a state when the detection chip 200 and the light source 120 are viewed from the detection unit 140 side is shown. As shown in FIG. 9A, in the present embodiment, when the plasmon scattered light β is detected, the light receiving range of the detection unit 140 is narrowed so that the end portion (stray light occurrence spot 41) of the first side wall 341 on the side of the storage portion does not fall within the detection range 40 of the detection unit 140, and the region corresponding to the irradiation spot 42 of the excitation light α falls within the detection range 40 of the detection unit 140. Therefore, the stray light occurrence spot 41 does not fall within the detection range 40, but the irradiation spot 42 of the excitation light α falls within the detection range 40. Therefore, the control unit 160 can obtain accurate data on the relationship between the incident angle of the excitation light α and the intensity of the plasmon scattered light β while preventing the influence of stray light derived from the excitation light α.

Figure 9B:
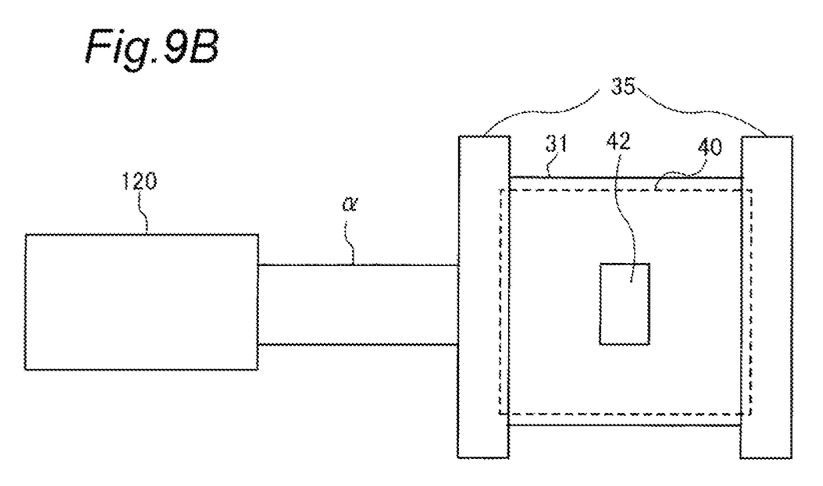
FIG. 9B is a schematic diagram showing a light receiving range of a detection unit and a position of a light source when a substance to be detected is detected in the detection device according to the second embodiment.

FIG. 9B is a schematic diagram showing the detection range 40 of the detection unit 140 and the position of the light source 120 when the fluorescence is measured. As shown in FIG. 9B, by expanding the detection range 40 of the detection unit 140 so that the end portions of the first side wall 341 and the second side wall 342 on the side of the storage portion fall within both sides of the detection range 40 and the irradiation spot 42 of the excitation light α falls within the vicinity of the center of the detection range 40, it is possible to efficiently and reproducibly detect the fluorescence from the reaction field (region where the capturing body is immobilized) on the metal film 31 and to improve the detection accuracy (accuracy, accuracy of absolute value) of the substance to be detected. Since the stray light occurring here has the same wavelength as the excitation light α, in the measurement of the optical blank value measured by inserting the excitation light cut filter 143 and the measurement of the specimen signal, the stray light 21 is not detected by the detection unit 140 and does not affect the measurement performance. Furthermore, since the irradiation spot 42 of the excitation light α falls within the vicinity of the center of the detection range 40, even if the irradiation spot 42 of the excitation light α and the detection range 40 varies due to setting variations of the detection chip 200 or the like, the fluorescence from the reaction field (region where the capturing body is immobilized) on the metal film 31 can be efficiently and reproducibly detected without the irradiation spot 42 of the excitation light α falling outside the detection range 40, and the detection accuracy (accuracy, accuracy of absolute value) of the substance to be detected can be improved.

As is clear from FIGS. 9A and 9B, the detection range 40 when the plasmon scattered light β is detected and the detection range 40 of the fluorescence when the fluorescence is detected have different sizes, and the detection range 40 of the detection unit 140 when the plasmon scattered light β is detected is smaller than the detection range 40 when the detection unit 140 detects the fluorescence.

(Effect)

As in the first embodiment, in the detection device and the detection method according to the present embodiment, the size of the light receiving range is different between the light receiving range at the time of detecting the plasmon scattered light in order to determine the enhancement angle and the light receiving range at the time of detecting the fluorescence in order to detect the presence or the amount of the substance to be detected. Thus, when the plasmon scattered light is detected in order to determine the enhancement angle, stray light derived from (diffracted light of) the excitation light is less likely to fall within the light receiving range of the detection unit, and the enhancement angle can be accurately determined. In addition, when the presence or the amount of the substance to be detected is detected, the maximum amount of fluorescence can be received, and the detection accuracy of the substance to be detected is improved.

INDUSTRIAL APPLICABILITY

The detection device and the detection method according to the present invention can more accurately determine the enhancement angle and improve the detection accuracy of the substance to be detected, and thus are useful for, for example, clinical examinations and the like.

The invention claimed is:

1. A detection device configured to detect presence or an amount of a substance to be detected using an enhanced electric field based on surface plasmon resonance, the detection device comprising:
   a chip holder configured to hold a detection chip including a prism having an incident surface and a film formation surface, a metal film disposed on the film formation surface, and a capturing body fixed on the metal film and configured to capture a substance to be detected;
   a light source configured to irradiate the metal film of the detection chip held by the chip holder with excitation light through the prism;
   a detection unit arranged to face the metal film of the detection chip held by the chip holder, the detection unit configured to detect light emitted from the metal film and a region on the metal film when the light source irradiates the metal film with the excitation light; and
   a detection range control unit configured to control a detection range of the detection unit in the metal film and the region on the metal film,
   wherein the detection range control unit controls a detection range of the detection unit so that a first detection range when the detection unit detects plasmon scattered light emitted from the metal film and the region on the metal film to determine an enhancement angle is different from a second detection range when the detection unit detects fluorescence emitted from a fluorescent substance that labels the substance to be detected captured by the capturing body.

2. The detection device according to claim 1, wherein the detection range control unit relatively moves a position of the detection range of the detection unit with respect to the detection chip held by the chip holder.

3. The detection device according to claim 2, wherein the detection range control unit moves the detection range of the detection unit by moving the detection chip held by the chip holder.

4. The detection device according to claim 2, wherein the detection range control unit moves the detection range of the detection unit by moving the detection unit.

5. The detection device according to claim 2, wherein the first detection range of is farther from the light source than the second detection range.

6. The detection device according to claim 5, wherein the irradiation position of the excitation light on the metal film when the detection unit detects the plasmon scattered light is farther from the light source than the irradiation position of the excitation light on the metal film when the detection unit detects the fluorescence.

7. The detection device according to claim 1, wherein the detection range control unit changes a size of the detection range of the detection unit.

8. The detection device according to claim 7, wherein the first detection range is smaller than the second detection range.

9. The detection device according to claim 1, wherein the detection chip includes:
   a wall portion disposed on the film formation surface or the metal film, the wall portion configured to define a storage portion for storing a liquid on the metal film, and
   an adhesive layer configured to adhere the film formation surface or the metal film to the wall portion.

10. The detection device according to claim 9,
    wherein the wall portion includes at least a first side wall and a second side wall facing each other,
    wherein the second side wall is farther from the light source than the first side wall, and
    wherein an end portion of the first side wall on a side of the storage portion does not fall within the first detection range.

11. The detection device according to claim 10, wherein an end portion of the second side wall on a side opposite to the storage portion does not fall within the first detection range.

12. The detection device according to claim 10,
    wherein the detection chip includes:
    a wall portion disposed on the film formation surface or the metal film, the wall portion configured to define a storage portion for storing a liquid on the metal film; and
    an adhesive layer configured to adhere the film formation surface or the metal film to the wall portion,
    wherein the wall portion includes at least a first side wall and a second side wall facing each other,
    wherein the second side wall is farther from the light source than the first side wall, and
    wherein, regarding a facing direction of the first side wall and the second side wall, a ratio (S/W) of a length (S) of an irradiation spot of the excitation light on the metal film to a distance (W) between the first side wall and the second side wall is more than 0.1 and less than 0.5.

13. The detection device according to claim 1,
further comprising a shape information acquisition unit configured to acquire shape information on the detection chip held by the chip holder,
wherein the detection range control unit determines the first detection range based on shape information on the detection chip acquired by the shape information acquisition unit.

14. The detection device according to claim 1, further comprising a positional information detection unit configured to detect positional information on the detection chip held by the chip holder,
wherein the detection range control unit determines the first detection range based on detection chip positional information acquired by the positional information detection unit.

15. The detection device according to claim 14,
wherein the detection chip includes:
a wall portion disposed on the film formation surface or the metal film, the wall portion configured to define a storage portion for storing a liquid on the metal film; and
an adhesive layer configured to adhere the film formation surface or the metal film to the wall portion,
wherein the wall portion includes at least a first side wall and a second side wall facing each other,
wherein the second side wall is farther from the light source than the first side wall, and
wherein positional information on the detection chip includes positional information on at least one of the first side wall and the second side wall.

16. The detection device according to claim 1, wherein the first detection range is different from the second detection range in a position or size.

17. The detection device according to claim 1, wherein when the detection unit detects plasmon scattered light emitted from the metal film, a stray light occurrence spot of the excitation light does not fall within the first detection range, but the irradiation spot of the excitation light falls within the first detection range.

18. A detection method for detecting presence or an amount of a substance to be detected using an enhanced electric field based on surface plasmon resonance, the detection method comprising:
preparing a detection chip including:
a prism having an incident surface and a film formation surface;
a metal film disposed on the film formation surface; and
a capturing body fixed on the metal film and configured to capture a substance to be detected;
irradiating the metal film with excitation light through the prism and detecting plasmon scattered light emitted from the metal film and a region on the metal film to determine an enhancement angle; and
irradiating the metal film with the excitation light through the prism and detecting fluorescence emitted from a fluorescent substance that labels the substance to be detected captured by the capturing body,
wherein a first detection range of the plasmon scattered light when the plasmon scattered light is detected is different from a second detection range of the fluorescence when the fluorescence is detected.

* * * * *